United States Patent [19]

Borig et al.

[11] Patent Number: 4,881,532
[45] Date of Patent: Nov. 21, 1989

[54] ORTHOPEDIC HIP HINGE PROVIDING ADJUSTMENT FOR ABDUCTION

[76] Inventors: Donald A. Borig, 44 Pine Dr., Chester Springs, Pa. 00000; Godfrey Harris, 10676 W. Turfts Pl., Littleton, Colo. 00000; Gary P. Korngold, 3435 Fayance Pl., Thousand Oaks, Calif. 00000

[21] Appl. No.: 79,761

[22] Filed: Jul. 30, 1987

[51] Int. Cl.$^4$ .............................................. A61F 5/00
[52] U.S. Cl. ................................ 128/80 A; 128/80 F; 128/88
[58] Field of Search ................ 128/80 L, 87 R, 87 C, 128/80 A, 88, 80 F, 78; 16/224, 239, 343, 344

[56] References Cited

U.S. PATENT DOCUMENTS

| | | | |
|---|---|---|---|
| 799,503 | 9/1905 | Tripp | 16/239 |
| 2,857,783 | 10/1958 | Ranck et al. | 74/531 |
| 3,993,056 | 11/1976 | Rabischong et al. | 128/89 |
| 4,088,129 | 5/1978 | DiGiulio | 128/87 R X |
| 4,088,130 | 5/1978 | Applegate | 128/80 |
| 4,169,467 | 10/1979 | Rabischong et al. | 128/80 |
| 4,337,764 | 7/1982 | Lerman | 128/80 |
| 4,370,977 | 2/1982 | Mauldin et al. | 128/80 |
| 4,397,308 | 8/1983 | Hepburn | 128/88 |
| 4,467,792 | 8/1984 | Young et al. | 128/88 |
| 4,481,941 | 11/1984 | Rolfes | 128/80 C X |
| 4,502,472 | 3/1985 | Pansiera | 128/80 |
| 4,520,802 | 6/1985 | Mercer et al. | 128/80 |
| 4,559,935 | 12/1985 | Young et al. | 128/88 |

FOREIGN PATENT DOCUMENTS

| | | |
|---|---|---|
| 1324883 | 12/1963 | France . |
| 940767 | 7/1982 | U.S.S.R. ........................ 128/87 C |
| 2130488 | 6/1984 | United Kingdom . |
| 2177603 | 1/1987 | United Kingdom . |
| 2182714 | 5/1987 | United Kingdom . |

OTHER PUBLICATIONS

Seton Products, Inc., trade literature for "Seton Masterhinge Adjustabrace", SET-1856-1585RP, 1985.
Rohr & Co., Hilden Rhld., trade literature for Hip Orthoses, not dated, Catalog.
Orthotics Division of Hosmer, trade literature for "Cerebral Palsy Orthosis Kit", and Post-Op Total Hip Orthotic Joint, pp. 0-9 and 0-10.

Primary Examiner—Edgar S. Burr
Assistant Examiner—Moshe I. Cohen
Attorney, Agent, or Firm—Tilton, Fallon, Lungmus & Chestnut

[57] ABSTRACT

An orthopedic device suitable for controlling hip joints is provided which includes a first hinge means for flexion and extension of the hip and a second hinge means for abduction and adduction of the hip. The orthopedic hip hinge permits a shortening of the overall length of the hinge arm assembly during abduction of the hip and minimizes pistoning of the thigh attachment support. Also included with this invention are means for permitting free abduction of the orthopedic hinge within a specified range, while preventing any abduction of the hip. The disclosed device more closely approximates the actual motion of the femoral head in its socket, since the flexion hinge and the abduction hinge employ a common element, and are disposed in a ball-joint arrangement.

4 Claims, 1 Drawing Sheet

ORTHOPEDIC HIP HINGE PROVIDING ADJUSTMENT FOR ABDUCTION

FIELD OF THE INVENTION

This invention relates to orthoses for regulating the movement of an associate body part and, in particular, to orthopedic hip hinges that permit adjustments to be made to both the abduction-adduction axes and the extension-flexion axes of the hip.

BACKGROUND OF THE INVENTION

Hip joint orthoses have heretofore been employed by orthopedic professionals for a variety of problems including, Legg Calf Perthes Disease, brittle bone fractures, osteoarthritis, and post-operative therapy for total hip joint replacement. It is well known that hip hinges for casts and orthoses are employed to control abduction and adduction, flexion and extension, and loading of the femur. Most of the known techniques are designed to maintain the femoral head in its correct anatomical location and approximately normal orientation with respect to the acetabulum during the healing process. In most proscribed treatments, the patient is placed in some degree of abduction and the hip orthosis is adjusted to prevent adduction. Caution is taken to prevent adduction because it is known that such motion causes the femoral head to rotate out of its socket, increasing the likelihood of dislocation.

Traditionally, hip orthosis have included means for adjusting the flexion-extension axes of the hip joint while preventing lateral motion. See Rolfes, U.S. Pat. No. 4,481,941.

More recent devices have included two axes of motion arranged at right angles to one another. See Young et al, application GB 2163352A, published Feb. 26, 1986. The Young et al orthopedic hip hinge is equipped with a first flexion-extension axis that can be adjusted for limited motion and a second abduction-adduction axis having an adjustable locking means for setting the abduction at three different angular setting, namely, 0°, 15° and 30°. The second axis of Young et al can also provide free abduction when the shoulder pin is removed from the device. However, since adduction is not blocked, there is a chance that dislocation of the joint will occur, resulting in discomfort to the patient and the likelihood of more surgery. Moreover, the limitation of only three angular settings restricts the available positions for post operative treatment.

The Cerebral Palsy Orthosis by Hosmer® is designed to provide adjustable abduction to 25°, with free abduction beyond setting, thereby avoiding the risk of dislocation presented by Young et al. The Post-Op Total Hip Orthotic Joint, also by Hosmer®, has a 45° fixed flexion and abduction axis which can be pre-set to maintain positive medial pressure to the femoral head to prevent accidental dislocation of a prosthesis from the acetabular cup implanted in the ilium. The abduction axis is adjustable to 13° with a small wedge, and to 25° with a large wedge.

None of the prior art devices, however, provides for the gradual shortening of the overall length of the side bars, in conjunction with their hinges, referred hereinafter as "arm assembly", as the femoral head rotates and the distance between the hip and the thigh of the patient decreases with abduction. Since these appliances are relatively rigid along the length of the arm assembly, the shortening of the distance between the hip and the thigh causes sliding of the waist band and/or pistoning of the thigh attachment, resulting in discomfort to the patient. Although, Rolfes and others have provided for adjustments to the length of the control arms, these adjustments are fixed and are merely an accommodation for the height of the patient.

Accordingly, there is a need for an orthopedic hinge for use with hip joints that provides for variable control arm length as the distance between the hip and thigh of a patient decreases during abduction. There is also a need for an orthopedic hip hinge that provides free abduction within a limited range which also provides a greater degree of assimilation of the hip joint.

SUMMARY OF THE INVENTION

An orthopedic hinge suitable for supporting a hip is provided which includes an upper and a lower control arm. The device further employs a first hinge means for providing a range of rotation to the lower arm during flexion and extension of the hip and a second hinge means for providing a range of rotation to the lower arm during abduction and adduction of the hip. In an important aspect of this invention, the second hinge means includes a sliding pivot means for permitting a shortening of the arm assembly during abduction. The hinge can be adjusted to lock in the arm assembly at any angle of flexion or abduction within the provided ranges. Moreover, the hinge can be adjusted for free abduction motion up to the preferred 30° arc, while at the same time, preventing adduction.

Accordingly, an orthopedic hinge is provided with a greater availability of settings for fixing the abduction axis. More importantly, the hinge of this invention provides for the gradual receding of the lower control arm within the abduction hinge means during adduction to prevent sliding of the waistband or pistoning of the thigh attachment.

The abduction-adduction and flexion-extension axes of this invention are designed to overlap so that the hinge can closely approximate the behavior of the femoral head in its socket. By preventing adduction and through closer tracking of the hip joint, less discomfort will be experienced by patients utilizing this device.

It is, therefore, an object of this invention to provide an orthopedic device, of the kind suitable for hip casts and orthoses, having an arm assembly length that varies with the distance between the hip and the thigh during abduction.

It is another object of this invention to provide an orthopedic hinge that enables 5° increments of fixed abduction adjustments. It is another object of this invention to provide an orthopedic hinge that provides free abduction within provided range without adduction of the hip.

It is still another object of this invention to provide an orthopedic hinge which more closely approximates the movement of the femoral head within the acetabular cavity.

With these and other objects in view, which will become apparent to one skilled in the art as the description proceeds, this invention resides in the novel construction, combination, arrangement of parts and methods substantially as hereinafter described and more particularly defined in the attached claims.

BRIEF DESCRIPTION OF THE DRAWINGS

The accompanying drawings illustrate a complete embodiment of the invention according to the best mode for the best practical application of the principles thereof, and in which.

DESCRIPTION OF THE INVENTION

According to this invention, an orthopedic hinge of the type suitable for hip joints is provided having an upper and lower control arm forming an arm assembly with an overall length. This invention compensates for the shortening of the distance between a fixed point on the thigh and a fixed point on the patient's waist during abduction by providing an abduction hinge that rotates in much the same manner as the femoral head does in its socket. The novel hinges of this invention act in combination to provide a range of motion to the hip during walking and other activities which often include a combination of both abduction and flexion of the hip joint simultaneously. The preferred hinge provides fine tuning adjustments to the arc of abduction while preventing adduction and dislocation of the hip joint.

The orthopedic device 100 of this invention has an upper control arm for attaching the device 100 to a location on a patient's waist and a lower control arm (not shown) for attaching the device to a location on a patient's thigh. The orthopedic device 100 includes a first hinge means for providing a range of rotation to the lower arm during flexion and extension and a second hinge means for providing a range of rotation to the lower arm during abduction and adduction of the hip. The upper and lower control arms and the first and second hinge means form an arm assembly having an overall length. As the distance between a fixed point on the thigh and a fixed point on the patient's waist gets shorter during abduction, the second hinge means, through a sliding pivot means, permits a shortening of the overall length of the arm assembly. The device 100 further provides free abduction of the hip from about zero degrees to about ninety degrees, preferably from about zero degrees to about thirty degrees, when the preferred abduction locking means 18 is not employed.

Figure 1:
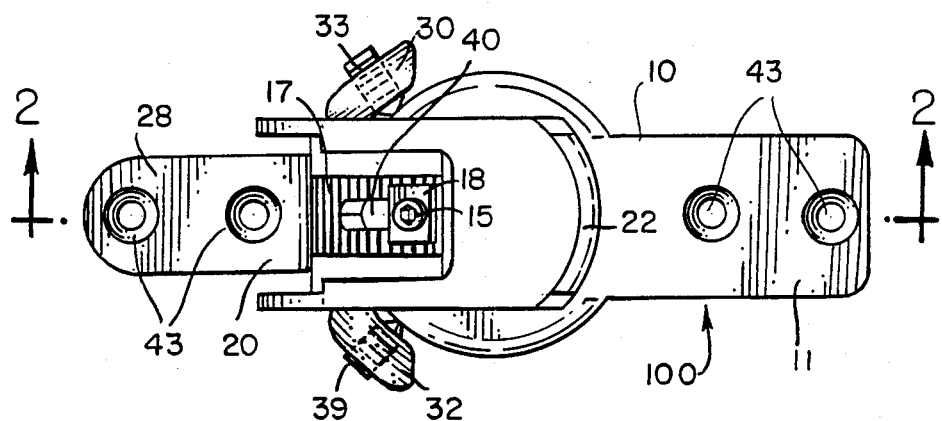
FIG. 1: is a top planar view of the orthopedic hinge of this invention in a locked position for both the flexion and abduction axes.
Figure 2:
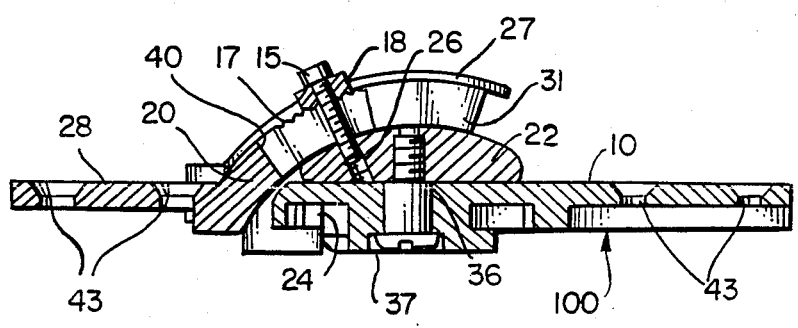
FIG. 2: is a transverse, cross-sectional view of the orthopedic hinge of FIG. 1 taken through line 2—2.

According to FIG. 1, the first hinge means includes a flexion hinge arm 10 having an extended portion 11 thereof for connecting the device 100 to the upper control arm. The upper hinge arm 10 also includes a track portion 24 disposed thereon, as depicted in FIG. 2. According to the preferred embodiment, the upper hinge arm 10 includes an aperture 37 therethrough for receiving a flexion swivel means 36, which provides an axis for flexion and extension for the device 100.

The preferred hip hinge of this invention provides for movement which corresponds closely to the motion of the femoral head within its socket. This is accomplished by positioning the flexion and abduction axis on top of one another, as opposed to stacking them vertically on the arm assembly, see Young et al, supra. This feature is facilitated by the preferred sliding pivot means which includes a pivot head means 22 rotatably mounted to the flexion hinge arm 10 through said swivel means 36. The preferred pivot head means 22 is designed with an outwardly-facing convex surface for acting as a bearing for the axis of abduction-adduction and a flat smooth surface for sliding against the flexion hinge arm 10 to provide the axis of flexion-extension. As indicated in FIG. 2, the radius of curvature of said pivot head means is great enough that the point about which such surface is generated is located well below upper arm 10, that is, well inwardly of the upper arm when the device is worn. The pivot head means 22 in combination with the abduction setting member 20 provide a "ball-and-socket-surface" for the second hinge means which provides a range of motion during abduction of the hip. This novel arrangement provides the shortening of the arm assembly and greatly facilitates simultaneous motion in both the abduction and flexion planes.

As described in FIG. 2, the pivot head means 22 preferably has an aperture 26 therein spaced laterally from the swivel means 36. This aperture 26, as will be discussed below, provides a means for fixing the abductive motion of the hip. The novel pivot head means 22 of this invention further comprises an abduction sleeve portion 27 having a concave surface disposed above said convex surface, as shown in FIG. 2. The concave and convex surfaces of the pivot head means 22 ideally form an abduction track 31.

The sliding pivot means of this invention further comprises an abduction setting member 20 disposed at least partially within said track 31 and slidably engaged with said convex surface of said pivot head means 22. Upon abduction of the hip, the adbuction setting member 20 slides over the pivot head means 22, thereby shortening the overall length of the arm assembly. Preferably, the abduction setting member 20 is also slidably engaged with the concave surface of the abduction sleeve portion 27 for accurately guiding abduction movement.

An important feature of this invention includes a slotted aperture 40 formed in the abduction setting member 20. To regulate abduction movement, an abduction locking means is disposed through said slotted aperture 40 and inserted into the aperture 26 of the pivot head means 22. The abduction control means is designed to limit the degree of free abduction provided by the device 100, and preferably is selected to be a threaded screw 15.

As described to this point, the hinge device 100 of this invention can provide free rotation of the flexion axis and limited free rotation of the abduction axis; the later providing from about zero to ninety degrees of free motion, preferably zero to thirty degrees of free motion. For locking the abduction axis, an abduction lock limiter 18 is disposed around the threaded screw 15 and engaged with the abduction setting member 20 when the threaded screw 15 is tightened. Preferably, the abduction lock limiter 18 comprises locking teeth for engaging the abduction setting member 20, and more preferably both the abduction lock limiter 18 and the abduction setting member 20 comprise teeth for fixing the degree of abduction of the hip. As used herein, the teeth associated with the abduction setting member 20 are referred to as "setting teeth" 17.

As in the case with the flexion hinge arm 10 of this invention, the abduction setting member 20 also preferably comprises an extended portion 28 for attachment to the lower control arm.

This invention additionally comprises novel means for fixing the degree of movement provided by the flexion axis. Pursuant to this object, a first flexion limiter 30 is disposed on the track portion 24 for contacting the abduction sleeve portion 27 to thereby limit the degree of flexion and extension of the hip. The preferred flexion limiter 30 comprises an adjustment screw 33 for fixing the flexion limiter 30 at a location on the flexion hinge arm 10.

Although a single flexion limiter 30 has been disclosed thus far, the most preferred embodiment includes a second flexion limiter 32 in addition to the first flexion limiter 30, for providing a means for fixing the degree of flexion of the hip. As in the case of the first flexion limiter 30, the second flexion limiter 32 comprises an adjustment screw 39 and preferably is disposed on the track portion 24. This limiter 32 can also be used for contacting the abduction sleeve portion 27. It is expected that the first and second flexion limiters 30 and 32 can provide a range of flexion and/or extension for the hip and, alternatively, can set the arc of flexion and/or extension at any point within a desired range. This range preferably is less than 180°, and more preferable is less than 140°.

The above-mentioned elements of this invention preferably are fabricated by conventional investment casting techniques using stainless steel raw materials, preferably AISI 303 stainless steel. The adjustable screws used herein are preferably machined from stainless steel stock. Although the upper and flexion control arms are not illustrated, they are preferably attached to the flexion hinge arm 10 and the abduction setting member 20 using fasteners applied through apertures 43, as is well known in the art. This is not a requirement, however, and it is anticipated that the upper control arm and flexion hinge arm 10 can be fabricated as one piece. Similarly, the lower control arm and the abduction setting member 20 can also be fabricated in one piece. In these embodiments, the first and second hinge means become integral with control arms. The preferred control arms should be made from a stainless steel, more preferably a stainless steel of the type commonly used for orthotic hinge arms.

The hinge device 100 of this invention can be easily adjusted to control the flexion axis by inserting a preferred allen wrench into the adjustment screws 33 and 39 having allen heads. These screws can be turned counter-clockwise until they are loose. The first flexion limiter 30 and/or the second flexion limiter 32 can then be pushed along the preferred track portion 24 and then tightened by locking the screws 33 and 39 by turning them clockwise. For locking the flexion axis, the above procedure can be followed, however, both the first and second flexion limiters 30 and 32 must contact the lower hinge arm simultaneously at the desired locked setting.

For locking the abduction axis, the preferred allen wrench is inserted into the more preferred threaded screw 15 and turned counter-clockwise until it is loose. Then the abduction lock limiter 18 is lifted and the abduction setting member 20 is positioned to the desired setting. The preferred locking teeth of the abduction lock limiter 18 is then engaged with the preferred setting teeth 17 of the abduction setting member 20 and the threaded screw 15 is tightened by turning it clockwise.

To provide free abduction motion to the hinge device 100, the preferred allen wrench is inserted into screw 15 and turned counter-clockwise until the screw is loose and can be removed from the device 100. Having done so, the abduction lock limiter 18 can be removed. By replacing the threaded screw 15 and tightening it by turning it clockwise, the preferred slotted aperture 40 will permit free abduction motion in the preferred range of about zero to about thirty degrees.

The use of this device 100 can be greatly facilitated by providing indicator means on the surfaces of the flexion hinge arm 10 and the abduction sleeve portion 27 representing degrees of setting for abduction and flexion-extension. Preferably, 5° abduction increments can be represented by markings provided on the abduction sleeve portion 27 and 5° flexion-extension increments can be provided on the flexion hinge arm 10.

From the foregoing it can be realized that this invention provides an improved orthopedic device suitable for hip casts and orthoses. This device provides better tracking of the hip joint and reduces pistoning of the support thigh attachment by continuously varying the length of the arm assembly during free abduction. Although various embodiments have been illustrated, this has been for the purpose of describing, but not limiting the invention. Various modifications, which will become apparent to one skilled in the art, are within the scope of this invention described in the attached claims.

We claim:

1. An orthopedic device of the kind suitable for hip casts and orthoses, comprising:
   (a) an upper arm for attaching said device to a location on a patient's waist;
   (b) pivot head means rotatably affixed to said upper arm for rotation about an axis alignable with the femoral head of such patient, said pivot head means having an outwardly-facing convex surface;
   (c) a lower arm for attaching said device to a location alongside a patient's thigh, said lower arm having a sleeve portion with an inwardly-facing concave surface slidably receiving said convex surface of said pivot head means for abductive and adductive movement of said lower arm;
   (d) said sleeve portion having a slot therein and said pivot head means being provided with control means secured thereto and extending through said slot for retaining said concave surface against said convex surface and for limiting the extent of said abductive and adductive movement.

2. The device of claim 1 in which said control means comprises a screw received in a threaded aperture in said pivot head means and extending through said slot; said screw having a head disposed outwardly beyond said sleeve portion; and abduction lock limiting means interposed between said head and said sleeve portion for engaging said sleeve portion and preventing abductive-adductive movement of said lower arm when said screw is tightened.

3. The device of claim 2 in which said sleeve portion and said abduction lock limiting means have mating teeth for adjustably securing said lower arm against abductive-adductive movement in a selected position of abduction.

4. The device of claim 1 in which adjustable limiting means are provided by said upper arm for engaging said lower arm and adjustably controlling the extent of flexion and extension about said axis.

* * * * *